United States Patent
Radley et al.

(10) Patent No.: US 9,459,218 B2
(45) Date of Patent: *Oct. 4, 2016

(54) METHOD FOR THE RADIOLOGICAL INVESTIGATION OF AN OBJECT

(75) Inventors: Ian Radley, Durham (GB); Ben Cantwell, Durham (GB); David Edward Joyce, Durham (GB); Paul Scott, Durham (GB)

(73) Assignee: Kromek Limited, Sedgefield (GB)

( * ) Notice: Subject to any disclaimer, the term of this patent is extended or adjusted under 35 U.S.C. 154(b) by 93 days.

This patent is subject to a terminal disclaimer.

(21) Appl. No.: 14/236,414

(22) PCT Filed: Aug. 1, 2012

(86) PCT No.: PCT/GB2012/051865
§ 371 (c)(1),
(2), (4) Date: Apr. 9, 2014

(87) PCT Pub. No.: WO2013/017879
PCT Pub. Date: Feb. 7, 2013

(65) Prior Publication Data
US 2014/0226788 A1 Aug. 14, 2014

(30) Foreign Application Priority Data
Aug. 1, 2011 (GB) .................................. 1113224.8

(51) Int. Cl.
*G01N 23/04* (2006.01)
*G01N 23/087* (2006.01)

(52) U.S. Cl.
CPC ............ *G01N 23/087* (2013.01); *G01N 23/04* (2013.01); *G01N 2223/423* (2013.01)

(58) Field of Classification Search
CPC ........... G01N 2223/423; G01N 23/04; G01N 23/087
See application file for complete search history.

(56) References Cited

U.S. PATENT DOCUMENTS

| 4,613,754 A | 9/1986 | Vinegar et al. |
| 5,600,303 A | 2/1997 | Husseiny et al. |

(Continued)

FOREIGN PATENT DOCUMENTS

| EP | 2377467 A1 | 10/2011 |
| EP | 2405260 A1 | 1/2012 |

(Continued)

OTHER PUBLICATIONS

Midgley, S. M., "A Parameterization Scheme for the X-Ray Linear Attenuation Coefficient and Energy Absorption Coefficient," Phys. Med. Biol. 49 (2004), pp. 307-325.

(Continued)

*Primary Examiner* — David J Makiya
*Assistant Examiner* — Dani Fox
(74) *Attorney, Agent, or Firm* — Winstead PC

(57) ABSTRACT

A method of identifying the material content of an object comprises: providing a radiation source and a radiation detector; irradiating a test object with radiation from the source; collecting at the detector system intensity data for radiation emergent from the test object; resolving the intensity data spectroscopically between a plural set of energy bands; numerically processing the spectroscopically resolved intensity data via the following steps: considering a material attenuation coefficient as a plural set of energy dependent polynomial equations in atomic number with a set of energy dependent coefficients across the said plural set of energy bands; determining a measured attenuation coefficient at each said energy band; calculating therefrom one or more orders of Compound Proton Number and/or effective mass thickness and/or density and for example a Compound Proton Number Set comprising plural order powers and preferably plural higher order powers of weighted compound atomic number.

14 Claims, 1 Drawing Sheet

(56) References Cited

U.S. PATENT DOCUMENTS

| | | | |
|---|---|---|---|
| 6,018,562 | A | 1/2000 | Willson |
| 2006/0233302 | A1 | 10/2006 | Might et al. |
| 2007/0030953 | A1 | 2/2007 | Sommer et al. |
| 2007/0263769 | A1 | 11/2007 | Roell |
| 2009/0086907 | A1 | 4/2009 | Smith |
| 2010/0002834 | A1 | 1/2010 | Gudmundson et al. |
| 2010/0172470 | A1 | 7/2010 | Kuwabara |
| 2010/0303287 | A1 | 12/2010 | Morton |
| 2011/0075800 | A1 | 3/2011 | Bjorkholm |
| 2014/0219419 | A1 | 8/2014 | Radley et al. |
| 2014/0297228 | A1 | 10/2014 | Radley et al. |

FOREIGN PATENT DOCUMENTS

| | | |
|---|---|---|
| GB | 2441551 A | 3/2008 |
| GB | 2454782 A | 5/2009 |
| JP | H06205767 A | 7/1994 |
| JP | 2009092658 A | 4/2009 |
| JP | 4614001 B2 | 1/2011 |
| WO | WO-2008034232 A1 | 3/2008 |
| WO | WO-2008040119 A1 | 4/2008 |
| WO | WO-2009046529 A1 | 4/2009 |
| WO | WO-2010086636 A2 | 8/2010 |

OTHER PUBLICATIONS

Midgley, S. M., "Materials Analysis Using X-Ray Linear Attenuation Coefficient Measurements at Four Photon Energies," Phys. Med. Biol. 50 (2005), pp. 4139-4157.

Midgley, S.M., "Measurements of the X-ray linear attenuation coefficient for low atomic number materials at energies 32-66 and 140keV", Radiation Physics and Chemistry, Elsevier Science Publishers BV, Amsterdam NL, vol. 72, No. 4, Mar. 1, 2005, pp. 525-535.

Okunade, A.A., "Parameters and computer software for the evaluation of mass attenuation and mass energy-absorption coefficients for body tissues and substitutes", Journal of Medical Physics, vol. 32, No. 3, 2007, pp. 124-132.

Kerur, B.R., et al., "Mass attenuation coefficient of saccharides for X-rays in the energy range from 8keV to 32keV", Radiation Measurements, Elsevier, Amsterdam, NL, vol. 44, No. 1, Jan. 1, 2009, pp. 63-67.

Han, I., et al., "Mass Attenuation coefficients, effective atomic and electron numbers of Ti and Ni alloys", Radiation Measurements, Elsevier, Amsterdam, NL, vol. 44, No. 3, Mar. 1, 2009, pp. 289-294.

Dedman, Emma, "International Search Report" for PCT/GB2012/051865, as mailed Jan. 17, 2013, 6 pages.

Dedman, Emma, "International Search Report," prepared for PCT/GB2012/051863, as mailed Dec. 21, 2012, 4 pages.

Jackson, Daphne F. et al., "X-ray Attenuation Coefficients of Elements and Mixtures", Physics Reports (Review Section of Physics Letters) 70, No. 3, 1981, pp. 171-233.

Kaneyasu, Tatsuo et al., "Dual-Energy X-ray CT by Compton Scattering Hard X-ray Source", Proceedings of 2005 Particle Accelerator Conference, IEEE, 2005, pp. 1291-1293.

Dedman, Emma, "International Search Report," prepared for PCT/GB2012/051864, as mailed Jan. 11, 2013, 4 pages.

U.S. Appl. No. 14/236,408, Radley.

U.S. Appl. No. 14/236,277, Radley.

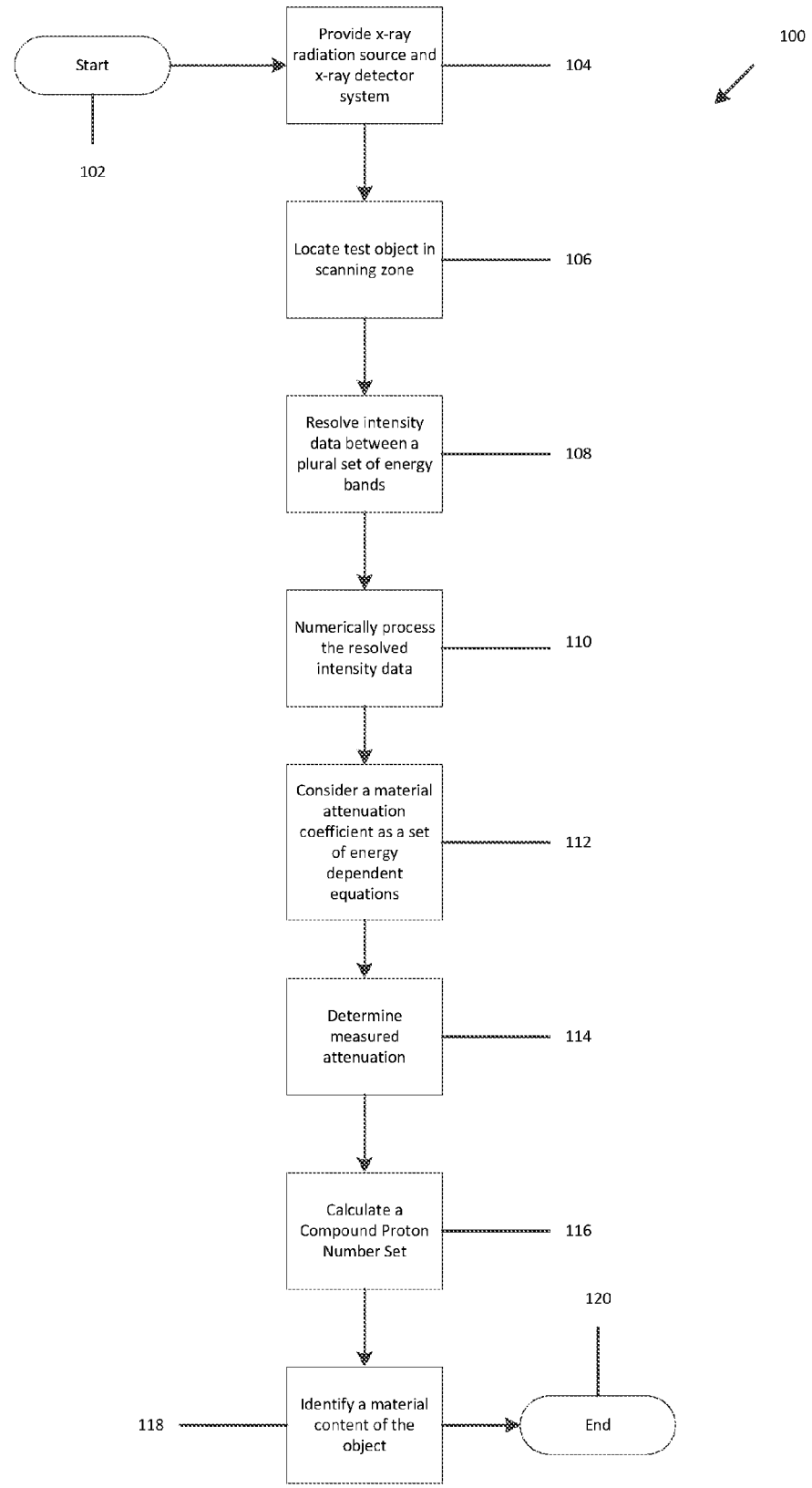

METHOD FOR THE RADIOLOGICAL INVESTIGATION OF AN OBJECT

This invention relates to a method for the radiological investigation of an object in particular using X-rays, and to a method of processing of detected radiation data from such a radiological examination.

This invention relates in particular to the creation of a set of compound-specific parameters, including in certain embodiments data representative of mass thickness, and including in certain embodiments data representative of multiple orders of weighted atomic number which we call herein a Compound Proton Number Set. In their infinite form such numbers identify and depend upon the composition of a compound. The invention in a particular embodiment includes a method for calculating a number and preferably a high number of dimensions of the Compound Proton Number Set using X-ray measurements measured at multiple energies, as a method for material identification.

The invention may in particular facilitate the detection of the presence of and/or classification or identification of particular target materials within a test object, for example materials which might represent a threat to security, a breach of customs regulations or the like.

The invention may in particular relate to a method and apparatus making us of a semiconductor detector device comprising a large direct band gap semiconductor material, for example a group II-VI semiconductor material such as cadmium telluride (CdTe), cadmium zinc telluride (CZT), cadmium manganese telluride (CMT) or the like, for example formed as a bulk single crystal but is not limited to any particular class of detectors.

It is desirable to scan the contents of objects at security and customs checkpoints to gain information about content, for example to obtain an indication that the contents of the object do not constitute a threat to security or a breach of customs regulations. It is also desirable to scan the contents of objects for other purposes such as quality control, content verification, degradation monitoring etc.

It is known that information useful in this regard may be obtained from a spectroscopic analysis of radiation received at a detector after interaction with an object under test for example by scanning the object from a suitable high energy electromagnetic radiation source, collecting emergent radiation at a suitable detector after interaction with the object, and processing the emergent radiation spectroscopically, for example against reference data, to draw conclusions about the composition of the object.

The Beer-Lambert law states that for a beam of photons of energy E with intensity $I_0$ incident on a material with thickness, t (cm), the intensity that emerges is $$I = I_0 e^{-\mu t} \quad 1$$

where $\mu$ is the linear attenuation coefficient and is defined as the probability of interaction per unit distance travelled. This has units of $cm^{-1}$. It is often preferable to work with a mass attenuation coefficient which is the linear attenuation coefficient ($\mu$) divided by the material density ($\rho$). The mass attenuation coefficient $$\left(\frac{\mu}{\rho}\right)$$

therefore has the units $g^{-1} cm^2$. The mass attenuation coefficient, in X-ray physics is also generally denoted by the symbol $\alpha$, not to be confused with the fine structure constant which also shares this symbol. As used herein $\alpha$ refers to the mass attenuation coefficient, unless otherwise specified. Therefore the Beer-Lambert law exnressed in terms of the mass attenuation coefficient is $$I = I_0 e^{-\frac{\mu}{\rho}(\rho t)} = I_0 e^{-\alpha(\rho t)} \quad 2$$

where the product of the density and the distance ($\rho t$) is defined as the mass thickness, x.

X-rays interact with the matter in a number of ways, which may lead to attenuation of the beam. The three most important methods of interaction are;

Compton Scattering
Photoelectric Effect
Pair production

Other effects, such as Thompson Scattering, play a smaller role, but which process dominates depends upon the mass absorption characteristics of the medium, which is in turn dependent upon the energy of the photons.

Which of these processes dominates is dependent on the mass absorption characteristics of the target (directly related to the atomic number, Z) and the energy of the X-ray shown schematically in FIG. 1.

At low energies the Photoelectric Effect tends to dominate the linear absorption coefficient ($\mu_\lambda$), as the photon energy increases the Compton Effect starts to dominate, until Pair Production occurs and dominates at energy above 1022 keV. As X-ray applications generally use X-ray up to several hundred keV, Pair Production does not occur and the attenuation of the beam is mainly caused by a combination of the other two effects.

Several attempts have been made to accurately describe the attenuation from an element, but all are approximations to real data which make a number of assumptions. One of the most widely accepted texts by Jackson and Hawkes, (D F Jackson and D J Hawkes, X-ray attenuation coefficients of elements and mixtures; Physics Reports 70 (3) pp169-233 (1981)), present a method for estimating the linear attenuation coefficient as $$\mu(Z, E) \cong \rho \frac{N_A}{A} Z \left\{ 4\sqrt{2} Z^4 \alpha^4 + \left(\frac{mc^2}{E}\right) \phi_0 \sum_{nll'} f_{nll'} + \sigma_{KN} + \frac{Z(1-Z^{b-1})}{Z'^2} \sigma_{SC}^{coh}(Z', E') \right\} \quad 3$$

where $\rho$ is the mass density, $N_A$ is Avagadro's number, A is the atomic mass, Z the atomic number, $\alpha$ in this case is the fine structure constant, m the electron rest mass, c the speed of light, $\phi_0$ is the Thomson classical cross section per atom, $f_{nll'}$ is a collection of terms for the Photoelectric cross section, $\sigma_{KN}$ is the Compton cross section and $\sigma_{SC}^{coh}$ is the Rayleigh scattering cross section of a standard element Z' at energy $$E' = \left(\frac{Z'}{Z}\right)^{1/3} E.$$

The fitting parameter b is material dependent, thus the exponent of the atomic number varies.

The Jackson Hawkes method has proved accurate in determining the atomic number of elements, but this approach has limitations as it does not directly lead to quantitative information on the composition of the mixture under investigation. Additionally, the definition of only one effective atomic number, often called $Z_{eff}$, characterising a material is not valid over wide energy ranges or crucially for mixtures or assemblies containing elements with different atomic numbers. This gives inaccuracies when measuring compounds materials, and does not provide discrimination of compounds which may be engineered to look similar in this one property. This method does provide a useful approximation for some radiation studies, however the functionality is limited.

For a more complete understanding of the present invention and for further objects and advantages thereof, reference may now be had to the following description taken in conjunction with the accompanying drawings in which:

FIG. 1 is a flow diagram of a method of obtaining x-ray radiation interaction data from an object.

In accordance with the invention in its most general concept a method of obtaining radiation interaction data from an object comprises:

providing a radiation source and a radiation detector system spaced therefrom to define a scanning zone therebetween;

locating a test object in the scanning zone; irradiating with radiation from the source; and collecting at the detector system intensity data for radiation emergent from the test object;

resolving the intensity data spectroscopically between a plural set of energy bands across the radiation spectrum;

numerically processing the spectroscopically resolved intensity data via the following steps:

considering a material attenuation coefficient as a plural set of energy dependent polynomial equations with a set of energy dependent coefficients across the said plural set of energy bands;

determining a measured attenuation coefficient at each said energy band;

calculating therefrom one or more orders of Compound Proton Number and/or effective mass thickness and/or density and for example a Compound Proton Number Set comprising plural order powers and preferably plural higher order powers of weighted compound atomic number;

making the one or more orders of Compound Proton Number and/or effective mass thickness and/or density and for example the Compound Proton Number Set available for the purposes of identifying the material content of the object.

Preferably the method comprises calculating at least two of: one or more orders of Compound Proton Number and/or effective mass thickness and/or density; and for example at least two orders of Compound Proton Number as a Compound Proton Number Set.

As has been defined herein, a Compound Proton Number Set comprises multiple orders of weighted compound atomic number. In their infinite form such numbers identify and depend upon the composition of a compound. The invention includes a method for calculating a number and preferably a high number of dimensions of the Compound Proton Number Set using X-ray measurements measured at multiple energies, as a method for material identification.

The invention comprises calculating one or more orders of Compound Proton Number and/or effective mass thickness and/or density and in the preferred case comprises calculating a Compound Proton Number Set as so defined, and making such data available for the purposes of identifying the material content of the object. Where use of such data is discussed herein, then except where the context necessarily requires otherwise the invention should be considered applicable to the use of one or more orders of Compound Proton Number and/or effective mass thickness and/or density in the general case and at least one Compound Proton Number Set as above defined in the preferred case.

The step of considering a material attenuation coefficient as a plural set of energy dependent polynomial equations comprises defining a numerical relationship comprising such a plural set of energy dependent polynomial equations with a set of energy dependent coefficients across the said plural set of energy bands, and for example making use of the formula of the general form:

$$\alpha(E) = a(E) + c(E)Z^2 + d(E)Z^3 \ldots + y(E)Z^n$$

in particular for plural higher order powers and for example at least the second and third powers. Plural powers and in particular plural higher order powers of this general form are preferred. Although plural powers and in particular plural higher order powers of this general form are preferred the invention does not exclude making use of single orders of Z.

The step of numerically processing the spectroscopically resolved intensity data items to determine a further spatially resolved dataset of data items representative of a mass thickness, may be included in the process to gather the Compound Proton Number Set.

The radiation source preferably comprises one or more sources to deliver high-energy radiation such as ionizing radiation, for example high energy electromagnetic radiation such as X-rays and/or gamma rays, or subatomic particle radiation, and the detection system is adapted correspondingly to detect radiation in this spectrum. The radiation source for example is a broadband source such as a broadband X-ray or gamma-ray source capable of producing broad spectrum emission over a wide range of energies. Additionally or alternatively, multiple sources may be used to produce such a broad spectrum emission over a wide range of energies. The source(s) are such as to enable an object under test to be irradiated across a broad enough spectrum to facilitate the resolution of the emergent intensity data into plural intensity bins as required for the subsequent data processing steps.

The invention is applied to dual and/or multispectral techniques and systems where emergent intensity data is resolved spectroscopically between at least two energy bands and more preferably at least three energy bands simultaneously and/or successively. A data collection step preferably comprises resolving the intensity data items spectroscopically between at least two energy bands and more preferably at least three energy bands across the spectrum of the source simultaneously and/or successively. Dual/multispectral techniques give more detailed information on which the numerical processing steps of the method in particular can work to provide data characteristic of the composition of the object. While multispectral techniques are ideally suited to such analysis techniques it will be clear to those skilled in the art that modifications of such techniques can be applied to, for example, dual energy detection systems.

The method of the invention accepts the complexity of the attenuation inherent in multi-element compounds, and treat the attenuation coefficient as a set of energy dependent high order polynomial equations, with a set of energy dependent coefficients. As the number of energy levels is measured, higher orders of the atomic number can be included in the equation. If the coefficients can be measured accurately, these fits to plural powers and in particular higher order powers of atomic number (which have been called herein Compound Proton Numbers) can be calculated, and the Compound Proton Number Set created, from which the material may be identified. As is the case with fitting techniques, the accuracy of fitting increases with the number of independent measures. In the case of dual energy techniques, only two measurements across broad energy bands are available for fitting. The greater number of data points collections using multi-spectral detection methods thus increases the accuracy of this method.

With the absorption of elements a function of the atomic number, a single-value Compound Proton Number Set may be calculated for each element. Compounds of elements will have a higher-complexity attenuation dependent upon the higher order polynomials of weighted atomic number, and each compound will have a Compound Proton Number Set. If a solution for a range of powers (or orders) of Compound Proton Number is calculated, the value of Compound Proton Number will be different for each power (as is demonstrated later in equations 13-15), which is not the case for elements. The multiple fit parameters permitted by multi-spectral techniques allow the Compound Proton Numbers to be calculated for a range of orders, unlike for dual-energy techniques, thus providing greater knowledge of the whole Compound Proton Number Set thus better identification of the material.

In the preferred case of the invention, the method step of considering a material attenuation coefficient as a plural set of energy dependent polynomial equations with a set of energy dependent coefficients across the said plural set of energy bands comprises resolving at least two orders for the polynomial equations and for example at least two higher orders.

In the preferred case of the invention, the method step of calculating therefrom plural order powers of atomic number comprises calculating at least two higher order powers and for example at least the second and third powers.

The invention is applied to dual and/or multispectral techniques and systems where emergent intensity data is resolved spectroscopically between at least two energy bands and more preferably at least three energy bands simultaneously and/or successively.

The key to the invention is that collected intensity data is resolved spectroscopically between a plurality of energy bands across the incident spectrum, more preferably at least three, and more preferably a larger plurality. This resolution is used to determine one or more orders of Compound Proton Number and/or effective mass thickness and/or density and for example a Compound Proton Number Set as above described.

In order to effect this, a predetermined incident radiation spectrum is required across a breath of spectrum/range of energies broad enough to facilitate the resolution of the emergent intensity data into plural intensity bands as required for the subsequent data processing steps. Within this general requirement such energy bands may be broad or narrow to the point of tending to be single energies, and may be adjacent or be spaced apart, and may collectively encompass any part or all of the spectrum of one or more suitable sources.

It is not specifically pertinent to the invention how, by suitable combination of sources and detectors, such a spectroscopically resolved intensity dataset is generated.

One or more radiation sources may be used to generate a predetermined incident radiation spectrum of the desired breadth across the full breadth simultaneously or across parts thereof sequentially.

The resultant predetermined incident radiation spectrum of the desired breadth may be resolved into plural energy bands simultaneously for example in that the detector system preferably exhibits a spectroscopically variable response across at least a part of the source spectrum allowing spectroscopic information to be retrieved and allowing intensity information to be detected simultaneously at a plurality of, and for example at least three, differentiated energy bands across the spectrum of the source.

A detector system may be so adapted by provision of multiple detectors calibrated to different energies or by the provision of at least one detector adapted to produce spectroscopic resolution inherently in that it exhibits a direct spectroscopic response. In particular such a detector is fabricated from a material selected to exhibit inherently as a direct material property a direct variable electrical and for example photoelectric response to different parts of the source spectrum. Such a detector may be a dual energy detector adapted to distinguish between two energy levels within the incident spectrum, or may be a genuinely multi-spectral detector adapted to distinguish between three or more energy levels within the incident spectrum.

The principles may be combined to distinguish a larger plurality of energy bands. For example a detector system may be used comprising a plurality of detectors that exhibit a spectroscopically variable response across at least a part of the incident spectrum with such detectors additionally calibrated to different energies. In a specific case of such a concept plural dual energy detectors calibrated to different energies may be used in order to distinguish between more than two energy levels within the incident spectrum.

Additionally or alternatively the resultant predetermined incident radiation spectrum of the desired breadth may be resolved into plural energy bands sequentially, for example using multiple detectors sequentially and/or filters and/or cycling incident radiation frequency.

In the preferred case, a multispectral X-ray technique is employed in which emergent intensity data is resolved spectroscopically between at least three energy bands simultaneously. Access to a plurality of energy bins provides information which is inaccessible to a dual energy system in particular in resolving higher orders of Compound Proton Number. As noted, this may be effected by using plural dual energy detectors calibrated to different energies and/or by using one or more multispectral detectors adapted to distinguish between three or more energy levels within the incident spectrum Multispectral X-ray techniques whether using truly multispectral detectors, for example CdTe-type detectors, or using plural dual energy detectors calibrated to different energies, offer many advantages over traditional dual energy systems. For a dual energy system the two energy regions are not entirely discrete due to the non-zero probability of detection of high energy X-rays in the low energy detector and vice versa. In addition the cut off between high and low energy bins is not precise, resulting in an overlap between the two energy regions. The detectors used for such systems are generally scintillation detectors, which are typically operated in a current mode which records the product of the interaction rate and the charge per interaction. As such these systems do not provide a photon counting capability and instead simply give a measure of the total deposited energy.

Scintillator response times are also quite slow, resulting in blurring of images and a loss of spatial resolution owing to afterglow effects.

In contrast a CdTe multispectral detector operates in pulse mode which preserves the energy and timing of individual events. The system is therefore capable of simultaneous measurement of the energy of each detected X-ray which can be measured to an accuracy fundamentally limited only by the detector resolution. As such systems use only a single detector to measure all energies each energy bin is discrete in nature with no overlapping between bins.

A suitable detector for implementation of the invention comprises one or more detector elements of a semiconductor material adapted for high energy physics applications, such as a material able to act as a detector for high energy radiation, and for example high energy electromagnetic radiation such as X-rays or gamma rays, or subatomic particle radiation. The resultant device comprises at least one layer of such material and is thus a device adapted for high energy physics applications, and for example a detector for high energy radiation such as X-rays or gamma rays, or subatomic particle radiation. The method comprises the use of such a device.

The semiconductor device is preferably a detector device adapted to exhibit a spectroscopically variable response across at least a substantial part of the intended radiation spectrum in use. In particular the semiconductor material is used that exhibits inherently as a direct material property a direct variable electrical and for example photoelectric response to different parts of the radiation spectrum in use.

In a preferred embodiment the semiconductor material is formed as a bulk crystal, and for example as a bulk single crystal (where bulk crystal in this context indicates a thickness of at least 500 µm, and preferably of at least 1 mm).

In a preferred embodiment the semiconductor material may be selected from Group II-VI semiconductors and in particular may be selected from cadmium telluride, cadmium zinc telluride (CZT), cadmium manganese telluride (CMT), and alloys thereof, and for example, save for incidental impurities, consists essentially of crystalline $Cd_{1-(a+b)}Mn_aZn_b Te$ where $a+b<1$ and a and/or b may be zero. A composite device may also have other detector elements of other materials for additional functionality.

The invention in the first aspect comprises a method of obtaining radiation interaction data from an object, in particular X-ray interaction data from an object, which involves resolving one or more orders of Compound Proton Number and/or effective mass thickness and/or density and for example a Compound Proton Number Set as above described and making these data available for the purposes of identifying the material content of the object.

Measured data may be compared with library data for known materials. For example, the one or more orders of Compound Proton Number and/or an effective mass thickness and/or a density and for example the Compound Proton Number Set is made available for comparison against a database of datasets of one or more orders of Compound Proton Number and/or an effective mass thickness and/or a density and for example Compound Proton Number Set for a range of known materials and the method in the preferred embodiment comprises the step of comparing a measured Compound Proton Number Set against a library database of such known equivalent data.

In a preferred case for example the method may be applied to facilitate the detection of the presence of and/or classification or identification of particular target materials within a test object, for example materials which might represent a threat to security, a breach of customs regulations or the like.

In such a case, a library database comprising such data and for example at least Compound Proton Number Sets for a range of such threat materials is provided, and the comparison step comprises comparing measured and derived data and for example Compound Proton Number Sets for an object under test against such a database.

In accordance with the invention, radiation emergent from the test object is processed at least spectroscopically between a plural set of energy bands across the spectrum of the source. The invention does not preclude further processing and sub-division of the data, for example for the purposes of spatial resolution, depth resolution, for generation of imaging information, or for any other desired purpose.

In the preferred case, the step of collecting at the detector system intensity data for radiation emergent from the test object comprises at least the step of collecting transmitted intensity data, and for example comprises a step of collecting only transmitted intensity data, and the numerical processing steps comprise determining therefrom an attenuation coefficient related to attenuation of transmitted intensity.

The invention finds particularly useful application in relation to the scanning of objects comprising containers of contained materials which by their nature will be expected to have a single generally homogeneous composition, for example fluid compositions such as liquids, including mixtures, solutions, emulsions, suspensions etc, like flowable compositions such as gels, pastes, creams, fine powders, and the like, aerosols etc. However, it should be understood that the invention is not limited to such liquids applications, and many of general principles of the invention may be equally applicable to hetereogenous objects with solid and/or liquid contents.

In accordance with the invention in a second aspect, a method of processing of detected radiation data from a radiological examination of an object comprises the numerical processing steps of the first aspect of the invention.

That is to say, a method of processing of data from a radiological examination of an object which has been resolved into plural energy bands comprises the steps of:
considering a material attenuation coefficient as a plural set of energy dependent polynomial equations with a set of energy dependent coefficients across the said plural set of energy bands;
determining a measured attenuation coefficient at each said energy band;
calculating therefrom one or more orders of Compound Proton Number and/or effective mass thickness and/or density and for example a Compound Proton Number Set comprising plural order powers and preferably plural higher order powers of compound atomic number.

Preferably the method comprises generating at least two of: one or more orders of Compound Proton Number and/or effective mass thickness and/or density; and for example at least two orders of Compound Proton Number as a Compound Proton Number Set.

The method is practiced on detected radiation data that spectroscopically between a plural set of energy bands and in particular preferably between at least three energy bands and in an initial step comprises providing such spectroscopically resolved data for numerical processing as above, and for example an initial step of resolving collected intensity data spectroscopically between a plural set of energy bands and in particular preferably between at least three energy bands.

The method conveniently further comprises making the one or more orders of Compound Proton Number and/or effective mass thickness and/or density and for example the Compound Proton Number Set available for the purposes of identifying the material content of an object under test.

The method of the second aspect thus comprises at least the numerical processing steps of the method of the first aspect, and further preferred features and embodiments will follow by analogy.

It will be understood generally that each numerical step in the method of the invention can be implemented by a suitable set of machine readable instructions or code. These machine readable instructions may be loaded onto a general purpose computer, special purpose computer, or other programmable data processing apparatus to produce a means for implementing the functions specified.

These machine readable instructions may also be stored in a computer readable medium that can direct a computer or other programmable data processing apparatus to function in a particular manner, such that the instructions stored in a computer readable medium produce an article of manufacture including instruction means to implement some or all of the steps in the method of the invention. Computer program instructions may also be loaded onto a computer or other programmable apparatus to produce a machine capable of implementing a computer executed process such that the instructions are executed on the computer or other programmable apparatus providing steps for implementing some or all of the steps in the method of the invention. It will be understood that a step can be implemented by, and a means of the apparatus for performing such a step composed in, any suitable combinations of special purpose hardware and/or computer instructions In accordance with the invention in a third aspect there is provided at least one computer program comprising program instructions which when loaded onto a suitable computer will cause the computer to perform one or more and for example all of the numerical processing steps of the method of the first aspect of the invention or one or more and for example all of the numerical processing steps of the method of the second aspect of the invention.

The at least one computer program may without limitation be embodied on a computer-readable recording medium or read-only memory, stored in a memory of a computer, stored in a remote memory accessible by a computer for example via a distributed network, or carried on a suitable carrier signal.

An embodiment of a possible numerical analysis method in accordance with the invention will now be discussed by way of example only with reference to FIG. 1 of the drawings which is a schematic diagram of the dominant interaction modes as a function of energy and atomic number.

Expressed numerically, from the Compound Proton Number Set, we define the Compound Proton Number of order n as $_{CPN}^{n}Z$. A preferred Compound Proton Number Set comprises at least n=2, n=3.

One simple embodiment of the method which has been used for material identification is to use three energy bins, and using the following approximation for the mass attenuation coefficient for all elements:

$$\alpha(E) = a(E) + c(E)Z^2 + d(E)Z^3 \qquad 4$$

For a compound material the mass attenuation coefficient is given by the sum of the individual attenuation coefficients ($\alpha_i$) weighted by their mass fraction, $w_i$, so that $$\alpha_{compound} = \sum_i w_i \alpha_i \qquad 5$$

Therefore:

$$R(E) = \ln(I_0(E)/I(E)) = x \sum_j w_j (a(E) + c(E)Z_j^2 + d(E)Z_j^3) \qquad 6$$

where $w_j$ is the mass fraction of the element j within the material under investigation.

Rearranging Equation 6 gives:

$$R(E) = x\left[a(E)\sum_j w_j + c(E)\sum_j w_j Z_j^2 + d(E)\sum_j w_j Z_j^3\right] \qquad 7$$

So $$R(E) = x\left[a(E) + c(E)\overline{Z^2} + d(E)\overline{Z^3}\right] \qquad 8$$

where $\overline{Z^2}$ and $\overline{Z^3}$ are the simple weighted mean square and mean cube of the atomic number respectively. Here, the second order Compound Proton Number $$_{CPN}^{2}Z = \sqrt[2]{(\overline{Z^2})}$$

and the third order Compound Proton Number $$_{CPN}^{3}Z = \sqrt[3]{(\overline{Z^3})}$$

The components a(E), c(E) and d(E) can be found empirically either by experiment or by simulation in Geant4. This is done by carrying out I and $I_0$ measurements on a range of calibration items of known atomic mass and mass thickness. Equation 8 can then be solved for coefficients a(E), c(E) and d(E) across the energy bins.

The simplest way of doing this fit is to use just three energy bins, which we label 1, 2 and 3. To shorten the equations we define $R_{Energy\ Bin\ 1} = R_1$, $a_{Energy\ Bin\ 3} = a_3$, etc. Then we rewrite equation 8 for the three energy bins to get the simultaneous equations;

$$R_1 = x[a_1 + c_1\overline{Z^2} + d_1\overline{Z^3}]$$

$$R_2 = x[a_2 + c_2\overline{Z^2} + d_2\overline{Z^3}]$$

$$R_3 = x[a_3 + c_3\overline{Z^2} + d_3\overline{Z^3}] \qquad 9$$

This is a matrix equation. If we know the matrix $$M = \begin{pmatrix} a_1 & c_1 & d_1 \\ a_2 & c_2 & d_2 \\ a_3 & c_3 & d_3 \end{pmatrix} \qquad 10$$

then we can invert it and multiply $M^{-1}$ by three measured R values to get the vector $(x, x\overline{Z^2}, x\overline{Z^3})$ for the material sample. This allows us to obtain the second and third orders of the Compound Proton Number Set in this embodiment, along with the mass thickness, x. The matrix M depends only on our choice of energy bins. Once we have found M we can use it for any material as long as our starting assumption of equation 4 is valid.

It would be possible to find M by taking numbers from the NIST database for example. But in reality it is better to base it on our own measurements of materials of known composition. This way we can expect that the biases of our measurement system will be (at least partly) absorbed into the matrix and when we apply it to our own measurements of an unknown material the measurement biases will be reduced. We refer to measurement of M as calibration. Calibration is particularly simple if we use pure elements. We measure the absorption in, say, energy bin 1 of samples of three different elements of atomic numbers $Z_A$, $Z_B$, $Z_C$ and mass thicknesses $x_A$, $x_B$ and $x_C$. The result is three simultaneous equations again $$R_1(Z_A)/x_A = a_1 + c_1 Z_A^2 + d_1 Z_A^3$$

$$R_1(Z_B)/x_b = a_1 + c_1 Z_B^2 + d_1 Z_B^3$$

$$R_1(Z_C)/x_c = a_1 + c_1 Z_C^2 + d_1 Z_C^3 \qquad 11$$

So once again we solve for $(a_1, c_1, d_1)$ by multiplying the vector of measured R/x values by $X^{-1}$, where $$X = \begin{pmatrix} 1 & Z_A^2 & Z_A^3 \\ 1 & Z_B^2 & Z_B^3 \\ 1 & Z_C^2 & Z_C^3 \end{pmatrix} \qquad 12$$

And repeat for the other two energy bins to get the whole of matrix M. The calibration elements can be any elements covering the range of atomic numbers likely to be encountered in the analysis e.g. carbon, aluminium and copper.

As a simple example to show how the second and third order Compound Proton Numbers will be different in a compound, but be the same in an element, consider a compound made up of two items in an atomic number of 2, and a second with an atomic number of 5, with a 50:50 combination by weight. Therefore, the second order Compound Proton Number $$^2_{CPN}Z = \sqrt[2]{\left(\frac{1}{2}2^2\right) + \left(\frac{1}{2}5^2\right)} = 3.81 \qquad 13$$

And for the third order Compound Proton Number $$^3_{CPN}Z = \sqrt[3]{\left(\frac{1}{2}2^3\right) + \left(\frac{1}{2}5^3\right)} = 4.05 \qquad 14$$

However for a single element of atomic number 5 both second and third order Compound Proton Numbers are identical (as indeed are any orders of Compound Proton Number).

$$^2_{CPN}Z = \sqrt[2]{(5^2)} = 5 = \sqrt[3]{(5^3)} = ^3_{CPN}Z \qquad 15$$

As each material will have a different set of Compound Proton Numbers, the greater the dimensions of the Compound Proton Number that can be calculated the more information about the material can be gathered, and the material better identified. Further orders will readily be derivable using the same basic principles of the invention and sufficient plural energy bins of radiation data.

As an example measured on real apparatus, the calculation of mass thickness and the ability to measure both $_{CPN}^2Z$ and $_{CPN}^3Z$ can be exploited in order to distinguish powdered aluminium from a solid aluminium block. The oxide content is significantly greater in powdered aluminium due to the increased surface area over that of a solid block of aluminium. This then results in a compound which can be identified by the difference between the $_{CPN}^2Z$ and $_{CPN}^3Z$. Additionally, with the aid of a tomographic thickness measurement, the density of the material can be derived by dividing the mass thickness by the measured thickness. Densities deviating significantly from that of a solid block of aluminium are clearly powders.

Table 1 shows the resulting density, $_{CPN}^2Z$ and $_{CPN}^3Z$. The $_{CPN}^2Z$ and $_{CPN}^3Z$ are identical for the aluminium block and the density is over 95% of that expected for a solid block. In contrast the powdered aluminium shows a variation in $_{CPN}^2Z$ and $_{CPN}^3Z$ indicating the sample is a compound rather than a single element and the densities of both powder samples are significantly lower than expected for a solid block of material.

TABLE 1

Second and third order Compound Proton Numbers, $_{CPN}^2Z$ and $_{CPN}^3Z$, measured for aluminium powder and an aluminium block. The density was derived here from knowledge of the physical thickness of the samples and measurement of the mass thickness.

| Material | Mass thickness (gcm$^{-2}$) | Thickness (cm) | Density (gcm$^{-3}$) | $_{CPN}^2Z$ | $_{CPN}^3Z$ | % of Expected Density |
|---|---|---|---|---|---|---|
| Al powder in an aluminium can | 3.08 | 6.5 | 0.47 | 12.71 | 11.65 | 17.55 |
| Al block 1.56 cm | 4.02 | 1.56 | 2.58 | 12.92 | 12.92 | 95.46 |

FIG. 1 is a flow diagram of a process 100 of obtaining x-ray radiation interaction data from an object. The process begins at step 102. At step 104, an x-ray radiation source and an x-ray radiation detector system are provided. The x-ray radiation source and the x-ray radiation detector system are spaced to define a scanning zone therebetween. At step 106, a test object is located in the scanning zone and irradiated with x-ray radiation from the x-ray radiation source. Intensity data for x-ray radiation emergent from the test object is collected at the x-ray detector system. At step 108, the intensity data is resolved spectroscopically between a plural set of energy bands. At step 110, the spectroscopically resolved intensity data is numerically processed. At step 112, a material attenuation coefficient is considered as a plural set of energy dependent polynominal equations with a set of energy dependent coefficients across the plural set of energy bands. At set 114, a measured attenuation is determined from the spectroscopically resolved intensity data at each energy band. At step 116, a Compound Proton Number Set is calculated comprising plural order powers of weighted atomic number from each measured attenuation. At step 118, the material content of the object is identified from the material attenuation and the Compound Proton Number Set. The process 100 ends at step 120.

The invention claimed is:

1. A method of obtaining x-ray radiation interaction data from an object comprising the steps of:
   providing an x-ray radiation source and an x-ray radiation detector system spaced therefrom to define a scanning zone therebetween;
   locating a test object in the scanning zone; irradiating with x-ray radiation from the source; and collecting at the detector system intensity data for x-ray radiation emergent from the test object;
   resolving the intensity data spectroscopically between a plural set of energy bands;
   numerically processing the spectroscopically resolved intensity data via the following steps:
      considering a material attenuation coefficient as a plural set of energy dependent polynomial equations with a set of energy dependent coefficients across the said plural set of energy bands;
      determining a measured attenuation from said spectroscopically resolved intensity data at each said energy band;
   calculating a Compound Proton Number Set comprising plural order powers of weighted atomic number from each measured attenuation the Compound Proton Number Set comprising solutions to the plural set of energy dependent polynomial equations; and
      identifying a material content of the object from the material attenuation and the Compound Proton Number Set.

2. A method in accordance with claim 1 wherein the source is an X-ray source, and the detection system is adapted correspondingly to detect and resolve X-rays between a plural set of energy bands.

3. A method in accordance with claim 1 wherein a detector system is provided that exhibits a spectroscopically variable response across at least a part of an incident spectrum allowing spectroscopic information to be retrieved and allowing intensity information to be detected simultaneously at a plurality of differentiated energy bands.

4. A method in accordance with claim 1 wherein emergent intensity data is resolved spectroscopically between at least three energy bands simultaneously.

5. A method in accordance with claim 4 wherein a detector system is provided comprising plural dual energy detectors calibrated to different energies in order to distinguish between more than two energy levels within an incident spectrum.

6. A method in accordance with claim 4 wherein a detector system is provided comprising at least one multi-spectral detector inherently adapted to distinguish between three or more energy levels within an incident spectrum.

7. A method in accordance with claim 1 wherein the method step of considering a material attenuation coefficient as a plural set of energy dependent polynomial equations with a set of energy dependent coefficients across the said plural set of energy bands comprises defining a numerical relationship comprising such a plural set of energy dependent polynomial equations with a set of energy dependent coefficients across the said plural set of energy bands.

8. A method in accordance with claim 1 comprising resolving at least two higher orders for the polynomial equations.

9. A method in accordance with claim 1 comprising providing library database of known Compound Proton Number Sets for a range of particular target materials and comparing measured and derived Compound Proton Number Sets for an object under test against such a database.

10. A method in accordance with claim 1 wherein the step of collecting at the detector system intensity data for x-ray radiation emergent from the test object comprises the step of collecting transmitted intensity data, and the numerical processing steps comprise determining therefrom an attenuation coefficient related to attenuation of transmitted intensity.

11. A method in accordance with claim 1 wherein a Compound Proton Number Set is collected of at least second and third orders.

12. A method in accordance with claim 11 wherein said second and third orders are respectively derived from attenuation coefficients according to the relationship $$\alpha(E)=a(E)+c(E)Z^2+d(E)Z^3.$$

13. A method of processing of data from a radiological examination of an object which has been resolved into plural energy bands comprising the steps of:
   considering a material attenuation coefficient as a plural set of energy dependent polynomial equations with a set of energy dependent coefficients across the said plural set of energy bands; and
   determining a measured attenuation at each said energy band; and
   calculating a Compound Proton Number Set comprising plural order powers of weighted atomic numbers from each measured attenuation the Compound Proton Number Set comprising solutions to the plural set of energy dependent polynomial equations; and identifying a material content of the object from the Compound Proton Number Set.

14. A computer program product comprising a non-transitory computer-usable medium having computer-readable program code embodied therein, the computer-readable program code adapted to by executed to implement the method of claim 1.

* * * * *